United States Patent
Connor

(12) 
(10) Patent No.: US 6,214,867 B1
(45) Date of Patent: *Apr. 10, 2001

(54) ANTICONVULSANT DERIVATIVES USEFUL IN TREATING ESSENTIAL TREMOR

(75) Inventor: Gregory S. Connor, Tulsa, OK (US)

(73) Assignee: Ortho-McNeil Pharmaceutical, Inc., Raritan, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/504,151

(22) Filed: Feb. 15, 2000

Related U.S. Application Data

(60) Provisional application No. 60/120,413, filed on Feb. 17, 1999.

(51) Int. Cl.[7] .................................................. A61K 31/35
(52) U.S. Cl. ............................................................ 514/455
(58) Field of Search ............................................. 514/455

(56) References Cited

U.S. PATENT DOCUMENTS

| | | | |
|---|---|---|---|
| 4,513,006 | * 4/1985 | Maryanoff et al. | 514/23 |
| 4,981,867 | 1/1991 | Prince . | |
| 5,387,700 | * 2/1995 | Maryanoff et al. | 549/387 |
| 5,735,693 | * 4/1998 | Shank | 514/454 |

FOREIGN PATENT DOCUMENTS

WO 99/44581   9/1999   (WO) .

OTHER PUBLICATIONS

Ataki, D., Souzer, D., Atay, T., Baybas, S and Arpaci, B, Misdiagnosis and treatment in juvenile myoclonic epilepsy, Siezure 7(1): 63–66, Feb. 1998.

Okuma, Y., Shimo., H., Hatori, T., Tanaka, S., Kondo, T. and Mizumo, Y., Familial Cortical Tremor with Epilepsy: an under–recognized familial tremor, Clinical Neurology and Neurosurgey 100(1): 75–78, Mar. 1998.

Uitti, R. J., Medical Treatment of essential tremor and Parkinson's Disease, Geriatrics 53(5): 46–48 and 53–57, May 1998.

Terada, K., Ikeda, A., Mima, T., Kimura, M., Nagahama, Y., Kamioka, Y., Murone, I., Kimura, J. and Shibasaki, H, Familial cortical myoclonic tremor as a uniqaue form of cortical reflex myoclonus, Movement Disorders 12 (3): 370–377, May 1997.

Shimojima, K., Iwata, S–I. and Nomoto, M., The effects of benzodiazepines and Ca–channel blockers on oxotremorine–induced tremors in mice, Journal of brain Science 23 (4): 261–27, 1997.

Wasielewski, P.G., et al., Pharmacological Treatment of Tremor, Movement Disorders 13 Supplement 3: 90–100 (1998).

\* cited by examiner

*Primary Examiner*—Raymond Henley, III

(57) ABSTRACT

Anticonvulsant derivatives useful in treating essential tremor are disclosed.

10 Claims, No Drawings

ANTICONVULSANT DERIVATIVES USEFUL IN TREATING ESSENTIAL TREMOR

CROSS-REFERENCE TO RELATED APPLICATION

This application claims priority from U.S. provisional application Ser. No. 60/120,413, filed Feb. 17, 1999, the contents of which are hereby incorporated by reference.

BACKGROUND OF THE INVENTION

Compounds of Formula I:

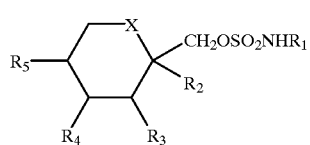

are structurally novel antiepileptic compounds that are highly effective anticonvulsants in animal tests (Maryanoff, B. E, Nortey, S. O., Gardocki, J. F., Shank, R. P. and Dodgson, S. P. *J. Med. Chem.* 30, 880–887, 1987; Maryanoff, B. E., Costanzo, M. J., Shank, R. P., Schupsky, J. J., Ortegon, M. E., and Vaught J. L. *Bioorganic & Medicinal Chemistry Letters* 3, 2653–2656, 1993). These compounds are covered by U.S. Pat. No. 4,513,006. One of these compounds 2,3:4,5-bis-O-(1-methylethylidene)-β-D-fructopyranose sulfamate known as topiramate has been demonstrated in clinical trials of human epilepsy to be effective as adjunctive therapy or as monotherapy in treating simple and complex partial seizures and secondarily generalized seizures (E. FAUGHT, B. J. WILDER, R. E. RAMSEY, R. A. REIFE, L. D. KRAMER, G. W. PLEDGER, R. M. KARIM et. al., *Epilepsia* 36 (S4) 33, 1995; S. K. SACHDEO, R. C. SACHDEO, R. A. REIFE, P. LIM and G. PLEDGER, *Epilepsia* 36 (S4 33, 1995), and is currently marketed for the treatment of simple and complex partial seizure epilepsy with or without secondary generalized seizures in approximately twenty countries including the United States, and applications for regulatory approval are presently pending in several additional countries throughout the world.

Compounds of Formula I were initially found to possess anticonvulsant activity in the traditional maximal electroshock seizure (MES) test in mice (SHANK, R. P., GARDOCKI, J. F., VAUGHT, J. L., DAVIS, C. B., SCHUPSKY, J. J., RAFFA, R. B., DODGSON, S. J., NORTEY, S. O., and MARYANOFF, B. E., *Epilepsia* 35 450–460, 1994). Subsequent studies revealed that Compounds of Formula I were also highly effective in the MES test in rats. More recently topiramate was found to effectively block seizures in several rodent models of epilepsy (J. NAKAMURA, S. TAMURA, T. KANDA, A. ISHII, K. ISHIHARA, T. SERIKAWA, J. YAMADA, and M. SASA, *Eur. J. Pharmacol.* 254 83–89, 1994), and in an animal model of kindled epilepsy (A. WAUQUIER and S. ZHOU, *Epilepsy Res.* 24, 73–77, 1996).

The conditions known as familial, essential and senile tremor cannot be distinguished on the basis of physiologic and pharmacologic properties. These are in the class of action tremors that oscillate with a frequency of about 4–8 hz, with variable amplitude. The familial form tends to be inherited as an autosomal trait and can begin in childhood, but typically onset is in adulthood and persists for life. If an inheritance pattern is not evident, the tremor is referred to as an essential tremor. Essential tremor also known as benign or idiopathic tremor begins early in adult life and persists. If tremor becomes evident in late life, it is known as a senile tremor. For purposes of the present application, the term "essential tremor" as used hereinafter, shall refer to and include familial, essential and senile tremor.

These are relatively common tremors with an estimated prevalence of 415 per 100,000 for people over age 40. Early on, the tremor may be limited to the upper extremities, particularly noticeable in the hands, but also may present as a nodding or side to side 'no' movement of the head. Typically, the tremor involves both head and upper extremities as the patient ages, but the lower extremities are spared. Frequently, the jaw, lips, tongue and larynx can be involved. The voice may quiver similar to that observed for Kathryn Hepburn.

Essential tremor is made worse by stimulants such as caffeine and by anxiety or stressful situations. The term 'benign' tremor can be misleading as even slight tremors may be disabling to a surgeon or fine craftsman or a tremor noticeable in public may be socially disturbing.

Treatments for essential tremor are currently available, but are limited due to their side effects and other problems. Alcohol is one of the oldest self-initiated therapies and it has been suggested that this may be a precipitant to alcoholism. Other sedatives are useful, particularly benzodiazepines and barbiturates, but these also have significant abuse potential and can be excessively sedating. Beta-blockers such as propranolol are the most accepted form of therapy but the response is quite variable. Propranolol appears to assist 50% of patients treated but it does not cure the tremor. However, adverse events such as impotence and depression can occur in many patients. The potential for cardiovascular side effects exist, including bradycardia, hypotension, arrhythmia and even cardiac arrest upon withdrawal. As such, beta-blockers must be used with great caution in the elderly. Notably, older patients seem to respond less requiring higher dosages in this population. Stereotactic neurosurgery to destroy a portion of the thalamus has been employed as treatment of last resort. Potential complications of this technique are numerous including difficulty with gait, speech and limb movements. (R. Adams, R. Victor, *Principles of Neurology*, McGraw Hill, 1989). Thus, a need remains for an effective treatment for essential tremor.

It is therefore an object of the invention to identify a method of treating essential tremor in a patient in need thereof. Still another object of the invention is to identify a method of treating essential tremor with fewer of the debilitating side effects present with current therapies.

DISCLOSURE OF THE INVENTION

Accordingly, it has been found that compounds of the following formula I:

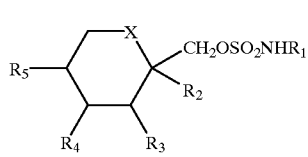

wherein X is O or $CH_2$, and R1, R2, R3, R4 and R5 are as defined hereinafter are useful in treating essential tremor.

DETAILED DESCRIPTION OF THE PREFERRED EMBODIMENTS

The sulfamates of the invention are of the following formula (I):

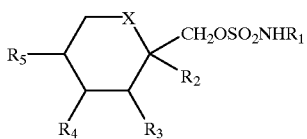

wherein

X is $CH_2$ or oxygen; $R_1$ is hydrogen or $C_1$–$C_4$ alkyl; and $R_2$, $R_3$, $R_4$ and $R_5$ are independently hydrogen or $C_1$–$C_3$ alkyl and, when X is $CH_2$, $R_4$ and $R_5$ may be alkene groups joined to form a benzene ring and, when X is oxygen, $R_2$ and $R_3$ and/or $R_4$ and $R_5$ together may be a methylenedioxy group of the following formula (II):

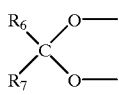

wherein $R_6$ and $R_7$ are the same or different and are hydrogen, $C_1$–$C_3$ alkyl or are alkyl and are joined to form a cyclopentyl or cyclohexyl ring.

$R_1$ in particular is hydrogen or alkyl of about 1 to 4 carbons, such as methyl, ethyl, iso-propyl, n-propyl, n-butyl, isobutyl, sec-butyl and t-butyl. Alkyl throughout this specification includes straight and branched chain alkyl. Alkyl groups for $R_2$, $R_3$, $R_4$, $R_5$, $R_6$ and $R_7$ are of about 1 to 3 carbons and include methyl, ethyl, iso-propyl and n-propyl. When X is $CH_2$, $R_4$ and $R_5$ may combine to form a benzene ring fused to the 6-membered X-containing ring, i.e., $R_4$ and $R_5$ are defined by the alkatrienyl group =C—CH=CH—CH=.

A particular group of compounds of formula (I) is that wherein X is oxygen and both $R_2$ and $R_3$ and $R_4$ and $R_5$ together are methylenedioxy groups of the formula (II), wherein $R_6$ and $R_7$ are both hydrogen both alkyl or combine to form a spiro cyclopentyl or cyclohexyl ring, in particular where $R_6$ and $R_7$ are both alkyl such as methyl. A second group of compounds is that wherein X is $CH_2$ and $R_4$ and $R_5$ are joined to form a benzene ring. A third group of compounds of formula (I) is that wherein both $R_2$ and $R_3$ are hydrogen.

A particularly preferred compound for use in the methods of the present invention is 2,3:4,5-bis-O-(1-methylethylidene)-β-D-fructopyranose sulfamate, known as topiramate. Topiramate has the following structural formula

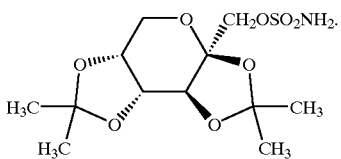

The compounds of formula (I) may be synthesized by the following methods:

(a) Reaction of an alcohol of the formula $RCH_2OH$ with a chlorosulfamate of the formula $ClSO_2NH_2$ or $ClSO_2NHR_1$ in the presence of a base such as potassium t-butoxide or sodium hydride at a temperature of about –20° to 25° C. and in a solvent such as toluene, THF or dimethylformamide wherein R is a moiety of the following formula (III):

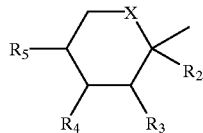

(b) Reaction of an alcohol of the formula $RCH_2OH$ with sulfurylchloride of the formula $SO_2Cl_2$ in the presence of a base such as triethylamine or pyridine at a temperature of about –40° to 25° C. in a solvent such as diethyl ether or methylene chloride to produce a chlorosulfate of the formula $RCH_2OSO_2Cl$.

The chlorosulfate of the formula $RCH_2OSO_2Cl$ may then be reacted with an amine of the formula $R_1NH_2$ at a temperature of abut 40° to 25° C. in a solvent such as methylene chloride or acetonitrile to produce a compound of formula (I). The reaction conditions for (b) are also described by T. Tsuchiya et al. in *Tet. Letters*, No. 36, p. 3365 to 3368 (1978).

(c) Reaction of the chlorosulfate $RCH_2OSO_2Cl$ with a metal azide such as sodium azide in a solvent such as methylene chloride or acetonitrile yields an azidosulfate of the formula $RCH_2OSO2N_3$ as described by M. Hedayatullah in *Tet. Lett.* p. 2455–2458 (1975). The azidosulfate is then reduced to a compound of formula (I) wherein $R_1$ is hydrogen by catalytic hydrogenation, e.g. with a noble metal and $H_2$ or by heating with copper metal in a solvent such as methanol.

The starting materials of the formula $RCH_2OH$ may be obtained commercially or as known in the art. For example, starting materials of the formula $RCH_2OH$ wherein both $R_2$ and $R_3$ and $R_4$ and $R_5$ are identical and are of the formula (II) may be obtained by the method of R. F. Brady in *Carbohydrate Research*, Vol. 14, p. 35 to 40 (1970) or by reaction of the trimethylsilyl enol ether of a $R_6COR_7$ ketone or aldehyde with fructose at a temperature of about 25° C., in a solvent such a halocarbon, e.g. methylene chloride in the presence of a protic acid such as hydrochloric acid or a Lewis Acid such as zinc chloride. The trimethylsilyl enol ether reaction is described by G. L. Larson et al in *J. Org. Chem. Volaa* 38, No. 22, p. 3935 (1973).

Further, carboxylic acids and aldehydes of the formulae RCOOH and RCHO may be reduced to compounds of the formula RCH2OH by standard reduction techniques, e.g. reaction with lithium aluminum hydride, sodium borohydride or borane-THF complex in an inert solvent such a diglyme, THF or toluene at a temperature of about 0° to 100° C., e.g. as described by H. O. House in *"Modern Synthetic Reactions"*, 2nd Ed., pages 45 to 144 (1972).

The compounds of formula I: may also be made by the processes disclosed in U.S. Pat. Nos. 4,513,006, and 5,387, 700, all of which are incorporated herein by reference. More particularly, topiramate may be prepared following the process described in Examples 1 to 3 of U.S. Pat. No. 5,387, 700.

The compounds of formula I include the various individual isomers as well as the racemates thereof, e.g., the various alpha and beta attachments, i.e., below and above the plane of the drawing, of $R_2$, $R_3$, $R_4$ and $R_5$ on the 6-membered ring. Preferably, the oxygen of the methylenedioxy group (II) are attached on the same side of the 6-membered ring.

The term "subject" as used herein, refers to an animal, preferably a mammal, most preferably a human, who has been the object of treatment, observation or experiment.

The term "essential tremor" as used herein, includes the conditions known as familial, essential and senile tremor.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

For treating essential tremor, a compound of formula (I) may be employed at a total daily dosage in the range of about 15 mg to about 500 mg, preferably, about 100 mg to about 400 mg, for an average adult human, administered one to four times per day, preferably, one to two times per day. A unit dose typically contains about 16 mg to about 300 mg, preferably, about 16 mg to about 200 mg, of the active ingredient.

Optimal dosages to be administered may be readily determined by those skilled in the art, and will vary with the particular compound used, the mode of administration, the strength of the preparation, the mode of administration, and the advancement or severity of the disease condition. In addition, factors associated with the particular patient being treated, including patient age, weight, diet and time of administration, will result in the need to adjust dosages.

To prepare the pharmaceutical compositions of this invention, one or more sulfamate compounds of formula (I) are intimately admixed with a pharmaceutical carrier according to conventional pharmaceutical compounding techniques, which carrier may take a wide variety of forms depending on the form of preparation desired for administration, e.g., oral, by suppository, or parenteral. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. Suppositories may be prepared, in which case cocoa butter could be used as the carrier. For parenterals, the carrier will usually comprise sterile water, though other ingredients, for example, for purposes such as aiding solubility or for preservation, may be included. Injectable solutions may also be prepared in which case appropriate stabilizing agents may be employed. Topiramate is currently available for oral administration in round tablets containing 25 mg, 100 mg or 200 mg of active agent. The tablets contain the following inactive ingredients: lactose hydrous, pregelatinized starch, microcrystalline cellulose, sodium starch glycolate, magnesium stearate, purified water, carnauba wax, hydroxypropyl methylcellulose, titanium dioxide, polyethylene glycol, synthetic iron oxide, and polysorbate 80.

The pharmaceutical compositions herein will contain, per dosage unit, e.g., tablet, capsule, powder injection, teaspoonful, suppository and the like from about 25 to about 200 mg of the active ingredient.

The following Examples are set forth to aid in the understanding of the invention, and are not intended and should not be construed to limit in any way the invention set forth in the claims which follow thereafter.

A retrospective analysis of seven patients treated in an open label manner with topiramate for essential tremor was performed. Characteristics of tremor, concomitant medications, duration of topiramate treatment, topiramate dose, response to treatment, and side effects were recorded. Patients were asked to rate percentage of improvement on a scale of 0 to 100%. Results from the seven patients studied showed subjective improvement in tremor ranging from 50 to 90% with doses of topiramate ranging from 100 to 400 mg per day and treatment duration from two to fourteen months with no significant side effects. This included improvement in postural, head and voice tremor.

EXAMPLE 1

Patient 01: Forty three year old female with tremor in hands for last ten years (handwriting and holding things are a problem). Had tried Inderal which caused depression. She had not tried anything else for tremor. Patient was started on topiramate on Sep. 30, 1998. At follow-up call on Oct. 30, 1998, patient reported >75%, perhaps 90%, improvement in tremor on topiramate 75 mg BID.

EXAMPLE 2

Patient 02: Female patient; had tried Mysoline, Blocadren, Effexor, Neurontin; on Aug. 20, 1997, she started topiramate in combination with other drugs; follow-up Dec. 15, 1997 indicated she was doing fantastic on topiramate with tremor at 150 mg BID; will taper Neurontin at this point. On Mar. 23, 1998, tremor still looks as good as last time, but she feels a little worse after stopping Neurontin, but she started Tranxene for anxiety and tremor also. Increased topiramate to 200 mg BID. On Jul. 15, 1998 she was doing fantastic with almost no postural tremor, still fair amount of tremor when writing. Patient has lost 50 pounds since starting topiramate. Continued on 200 mg BID topiramate and ½ of the mysoline. On Oct. 30, 1998, follow-up call revealed patient was under stress so tremor may be worse recently but overall improvement was rated as 60%.

EXAMPLE 3

Patient 03: Male patient with tremor primarily with head. He had failed two medications in past and on Aug. 11, 1998 he started topiramate treatment. During Sep. 11, 1998 follow-up call, he reported it was not really improving his tremor on 75 mg BID, so the dose was increased to 100 mg BID. At Oct. 30, 1998 follow-up, he reported 75% better on 100 mg BID.

EXAMPLE 4

Patient 04: 78 year old female with tremor never treated; also has seizure disorder. She had been on phenobarbital and doing well. Tried both Gabitril and Neurontin which haven't been tolerated or helped. On Apr. 29, 1998, since tremor was worse in both head and hand, patient was started on Mysoline. On May 27, 1998, she had seen no benefit and now was on 200 mg Mysoline, so treatment with topiramate was initiated. Once the topiramate dose reaches 50 mg BID, will taper off Mysoline. At Jun. 6, 1998 follow-up call, patient indicated she was better on topiramate 50 mg BID but room for more improvement, so increased topiramate to 75 mg BID. At Aug. 11, 1998 follow-up, patient was doing better with tremor at 75 mg BID. Patient still had some head tremor, but writing tremor was much better and people around her had noticed. Patient was tolerating treatment without any problems and will increase topiramate to 100 mg BID and now reducing Mysoline to hopefully stop this medication. At Aug. 25, 1998 follow-up, patient indicated not doing well—shaky and can't sleep, so topiramate was increased to 125 mg BID for 1 week, then 150 mg BID. On Sep. 30, 1998, patient called to report she was having more tremors so topiramate was increased to 200 mg BID. At Oct. 30, 1998 call, patient rated improvement of tremor 75% before mysoline was tapered, now improvement rated 50% on present dose of 200 BID topamax.

EXAMPLE 5

Patient 05: 40 year old female with tremor in hands and occasional voice. Had tried Inderal with not much help. Started Mysoline January 1997 and rated much better in March 1997. In June 1998, patient was having lots of hand shaking. At Jul. 14, 1998 visit, patient had problems with writing which caused difficulties due to her job as a teacher. Started topiramate at this visit. On Aug. 7, 1998, patient had seen some relief but not 100%. Some nausea problems with topiramate at 75 mg BID. Will switch topiramate treatment to 50 mg AM and 100 mg PM. On Oct. 6, 1998, she was rating 50% improvement and handwriting better. She is now able to teach without much problem. She would like to paint, so will increase topiramate. Patient is tolerating well with appetite suppression noted which she does not mind.

EXAMPLE 6

Patient 06: 43 year old female with tremor that has worsened over years, especially in hands (but head and whole body seem to shake at times). Never been on any medications specifically for tremor. Will try Mysoline May 1996. In November 1996, patient reported 50% improvement on Mysoline. In October 1997, tremor still 50% better but would like some better control; increasing Mysoline and if no benefit, will add Inderal. On Sep. 30, 1998, tremor still not satisfactory to her—still lot of writing problems and dissatisfied with Inderal due to fatigue, etc. Patient to start topiramate and if she does well, will stop Inderal. On Oct. 26, 1998, patient stated much improved, so stopped Inderal and increased topiramate to 100 mg BID. On Nov. 17, 1998, patient was doing much better and reported 75% improvement overall and tremor barely noticeable on postural testing. Some occasional paresthesias in hands, but not cognitive. Patient is off Inderal, but still on Mysoline.

EXAMPLE 7

Patient 07: 71 year old female with history of tremors in hands. Tried Corgard in 1993 but did not benefit from it. She has worsening of tremor when eating or writing. Started Mysoline in 1993. At September 1997 visit, patient indicated she was on topiramate at 25 mg BID with little change. Patient had some back problems causing her trouble at this time. She did not tolerate topiramate greater than 25 mg BID and she feels she has lost a little weight. Also starting Tranxene October 1997. In July 1998, off Mysoline and started Seligiline with another doctor. Over months, tremors were worsening. Back on Mysoline and stopped Seligiline. On Aug. 10, 1998, patient reported increase in trembling. She was not sure what medications was taking, so doctor started her on topiramate and Mysoline again. On Sep. 4, 1998, after restarting topiramate, patient was doing fantastic with 90% improvement in tremor and was very satisfied. Patient under much stress due to a fire. She was on 25 mg BID and we were going to try increasing to 50 BID gradually. On Oct. 29, 1998, patient was doing well on 50 mg topiramate BID and rated 75% improvement and loss of 12–14 pounds. Her family claims some memory loss, but doctor feels she is as sharp as always been.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A method for treating essential tremor in a subject in need thereof comprising administering to the subject a therapeutically effective amount of a compound of the formula I:

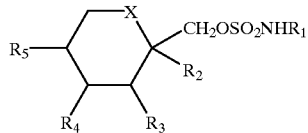

wherein
X is $CH_2$ or oxygen; $R_1$ is hydrogen or $C_1$–$C_4$ alkyl; and $R_2$, $R_3$, $R_4$ and $R_5$ are independently hydrogen or $C_1$–$C_3$ alkyl and, when X is $CH_2$, $R_4$ and $R_5$ may be alkene groups joined to form a benzene ring and, when X is oxygen, $R_2$ and $R_3$ and/or $R_4$ and $R_5$ together may be a methylenedioxy group of the following formula (II):

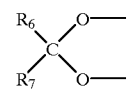

wherein $R_6$ and $R_7$ are the same or different and are hydrogen, $C_1$–$C_3$ alkyl or $R_6$ and $R_7$ together with the carbon to which they are attached are joined to form a cyclopentyl or cyclohexyl ring.

2. The method of claim 1, wherein the compound of formula I is topiramate.

3. The method of claim 1, wherein the therapeutically effective amount is from about 15 mg to about 500 mg per day.

4. The method of claim 1, wherein the therapeutically effective amount is from about 100 mg to about 400 mg per day.

5. The method of claim 1, wherein the compound is administered as a pharmaceutical composition.

6. A method of alleviating tremors in a subject in a subject in need thereof comprising administering to the subject a therapeutically effective amount of a compound of the formula I:

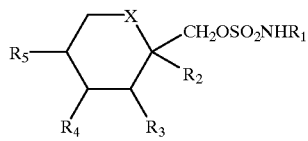

wherein
X is $CH_2$ or oxygen; $R_1$ is hydrogen or $C_1$–$C_4$ alkyl; and $R_2$, $R_3$, $R_4$ and $R_5$ are independently hydrogen or $C_1$–$C_3$ alkyl and, when X is CH2, R4 and $R_5$ may be alkene groups joined to form a benzene ring and, when X is oxygen, $R_2$ and $R_3$ and/or $R_4$ and $R_5$ together may be a methylenedioxy group of the following formula (II):

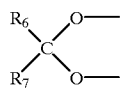

wherein $R_6$ and $R_7$ are the same or different and are hydrogen, $C_1$–$C_3$ alkyl or $R_6$ and $R_7$ together with the carbon to which they are attached are joined to form a cyclopentyl or cyclohexyl ring.

7. The method of claim 6, wherein the compound of formula I is topiramate.

8. The method of claim 6, wherein the therapeutically effective amount is from about 15 mg to about 500 mg per day.

9. The method of claim 6, wherein the therapeutically effective amount is from about 100 mg to about 400 mg per day.

10. The method of claim 6, wherein the compound is administered as a pharmaceutical composition.

\* \* \* \* \*